(12) United States Patent
Korth et al.

(10) Patent No.: US 8,129,556 B2
(45) Date of Patent: *Mar. 6, 2012

(54) PROCESS FOR PREPARING ORGANOSILANES

(75) Inventors: Karsten Korth, Grenzach-Wyhlen (DE); Ingo Kiefer, Schwörstadt-Dossenbach (DE); Alfred Alig, Geiselbach-Omersbach (DE); Ulrich Deschler, Sailauf (DE); Helmut Droege, Qingdao (CN); Sefan Koenigstein, Bochum (DE); Stephanie Schwan, Langen (DE)

(73) Assignee: Evonik Degussa GmbH, Essen (DE)

( * ) Notice: Subject to any disclaimer, the term of this patent is extended or adjusted under 35 U.S.C. 154(b) by 322 days.

This patent is subject to a terminal disclaimer.

(21) Appl. No.: 12/509,089

(22) Filed: Jul. 24, 2009

(65) Prior Publication Data

US 2010/0029971 A1 Feb. 4, 2010

(30) Foreign Application Priority Data

Jul. 31, 2008 (DE) .......................... 10 2008 035 623

(51) Int. Cl.
C07F 7/04 (2006.01)
(52) U.S. Cl. ...................................... 556/427
(58) Field of Classification Search ........................ None
See application file for complete search history.

(56) References Cited

U.S. PATENT DOCUMENTS

| 6,680,398 | B1 * | 1/2004 | Boswell et al. | 556/429 |
| 7,501,534 | B2 | 3/2009 | Korth et al. | |
| 2006/0204422 | A1 * | 9/2006 | Korth et al. | 423/325 |
| 2010/0217026 | A1 * | 8/2010 | Korth | 556/427 |

FOREIGN PATENT DOCUMENTS

| EP | 1700861 A1 | 9/2006 |
| WO | 2008025580 A1 | 3/2008 |
| WO | 2010/105434 A1 | 9/2010 |

OTHER PUBLICATIONS

Computer generated claim set translation of the earlier cited WO 2008025580, 2008 year.

* cited by examiner

*Primary Examiner* — Daniel Sullivan
*Assistant Examiner* — Yevegeny Valenrod
(74) *Attorney, Agent, or Firm* — Smith, Gambrell & Russell, LLP

(57) ABSTRACT

The invention relates to a process for preparing organosilanes of the general formula I

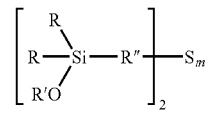

by reacting (haloorganyl)alkoxysilane of the formula II

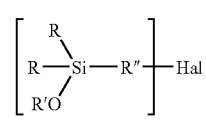

with hydrous alkali metal hydrogensulphide, sulphur and alkali metal carbonate in alcohol, wherein the molar (haloorganyl)alkoxysilane of the formula II to alkali metal hydrogensulphide ratio is between 1:0.4 and 1:0.75, and the molar alkali metal hydrogensulphide to alkali metal carbonate ratio is between 1:0.5 and 1:1.5.

8 Claims, No Drawings

PROCESS FOR PREPARING ORGANOSILANES

INTRODUCTION AND BACKGROUND

The invention relates to a process for preparing organosilanes.

EP 1130023 discloses the preparation of organosilyl-alkylpolysulphanes of the general formula $(R^1R^2R^3Si—R^4—)_2S_q$ from the organosilylalkyl halide of the general formula $R^1R^2R^3Si—R^4—X$. The reaction is performed by initially charging elemental sulphur and the organylalkyl halide in a polar organic solvent and adding anhydrous or virtually anhydrous ionic sulphide to this suspension. Owing to the proneness of the Si-alkoxy bonds of the organosilylalkyl halide to hydrolysis, the ionic sulphides must be anhydrous or virtually anhydrous.

EP 1700861 discloses the synthesis of sulphur-containing alkoxysilanes using hydrous sulphurizing reagents in alcohol. When different raw materials are used, great differences are found in the monomer content of the resulting polysulphidic alkoxysilanes. A reliable, homogeneous product quality on the industrial scale cannot be achieved in this way. In addition, the use of four solids in the known process is disadvantageous for the industrial scale.

WO 2008025580 A1 discloses preparing sulphur-containing alkoxysilanes of the general formula $[R(R)(R'O)Si—R''—]_2S_m$, wherein the alkali metal hydroxide content of all feedstocks must be <0.44% by weight.

Disadvantages of the known processes are either the use of anhydrous or virtually anhydrous starting materials or, in the case of hydrous starting materials, the strong dependence of the product properties on the raw material properties, especially the proportion of alkali metal hydroxides. In the known processes which use hydrous sulphurizing reagents, the use of more than 4 raw materials is undesired. Moreover, the metered addition and the use of alkali metal sulphide hydrate as a sulphurizing raw material is problematic, since solid alkali metal sulphide hydrates, as a result of the preparation, may contain relatively large amounts of alkali metal hydroxides. A low content of (mercaptoorganyl)alkoxysilane in the end product is desired.

SUMMARY OF THE INVENTION

It is an object of the present invention to provide a process for preparing polysulphidic organosilanes, which enables high conversions coupled with good selectivities, does not use any solid alkali metal sulphide hydrate and tolerates alkali metal hydroxide in the sulphurizing raw material.

The invention provides a process for preparing organosilanes of the general formula I

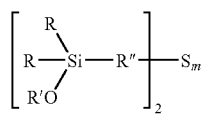

where

R is the same or different and is a $C_1$-$C_8$-alkyl, preferably $CH_3$ or $CH_2CH_3$, $C_1$-$C_8$-alkenyl, $C_1$-$C_8$-aryl or $C_1$-$C_8$-aralkyl group or an OR' group, R' is the same or different and is a $C_1$-$C_{24}$, preferably $C_1$-$C_4$ or $C_{12}$-$C_{18}$, more preferably $CH_2CH_3$, branched or unbranched monovalent alkyl or alkenyl group, an aryl group, an aralkyl group, hydrogen (—H), an alkyl ether group —$(CR^{III}_2)_{y'}$—O-Alk, where y'=1-20, preferably 2-10, more preferably 2-5, or an alkyl polyether group —$(CR^{III}_2O)_y$-Alk or —$(CR^{III}_2—CR^{III}_2—O)_y$-Alk, where y=2-20, preferably 2-10, more preferably 2-5, $R^{III}$ is independently H or an alkyl group, preferably $CH_3$ group, and Alk is a branched or unbranched, saturated or unsaturated, aliphatic, aromatic or mixed aliphatic/aromatic monovalent $C_1$-$C_{30}$ hydrocarbon group, preferably $C_2$-$C_{20}$, more preferably $C_6$-$C_{18}$, most preferably $C_{10}$-$C_{18}$, R" is a branched or unbranched, saturated or unsaturated, aliphatic, aromatic or mixed aliphatic/aromatic divalent $C_1$-$C_{30}$, preferably $C_1$-$C_{20}$, more preferably $C_1$-$C_{10}$, most preferably $C_1$-$C_7$, hydrocarbon group which is optionally substituted by F, Cl, Br, I, HS, $NH_2$ or NHR', and m is a mean sulphur chain length of 1.5 to 4.5, preferably 2 to 2.6 and 3.5 to 3.9, more preferably 2.1 to 2.3 and 3.6 to 3.8, by reacting (haloorganyl)alkoxysilane of the formula II

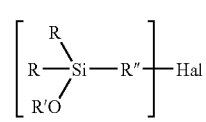

where R, R' and R" are each as defined above and Hal is chlorine, bromine, fluorine or iodine, with hydrous alkali metal hydrogensulphide, sulphur and alkali metal carbonate in alcohol, which is characterized in that the molar (haloorganyl)alkoxysilane of the formula II to alkali metal hydrogensulphide ratio is between 1:0.40 and 1:0.75, preferably between 1:0.45 and 1:0.65, more preferably between 1:0.5 and 1:0.6, most preferably between 1:0.5 and 1:0.55, and the molar alkali metal hydrogensulphide to alkali metal carbonate ratio is between 1:0.5 and 1:1.5, preferably between 1:0.65 and 1:1.3, more preferably between 1:0.85 and 1:1.2, most preferably between 1:0.95 and 1:1.1.

R" may be —$CH_2$—, —$CH_2CH_2$—, —$CH_2CH_2CH_2$—, —$CH_2CH_2CH_2CH_2$—, —$CH(CH_3)$—, —$CH_2CH(CH_3)$—, —$CH(CH_3)CH_2$—, —$C(CH_3)_2$—, —$CH(C_2H_5)$—, —$CH_2CH_2CH(CH_3)$—, —$CH_2CH(CH_3)CH_2$—or

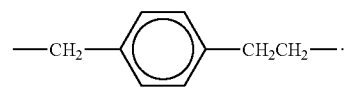

It has been found that, surprisingly, the water present in the sulphurizing reagents does not lead to complete hydrolysis and condensation of the alkoxysilanes, even though basic reaction conditions are present and, in stoichiometric terms, more water is present than is required to convert all SiOR present to SiOH and subsequently, by condensation, to corresponding siloxanes containing Si—O—Si bonds.

In the process according to the invention for preparing organosilanes, it is possible to form compounds of the general formula I or else mixtures of compounds of the general formula I.

Mixtures of organosilanes of the formula I may contain more than 50% by weight, preferably more than 60% by weight, more preferably more than 70% by weight, most preferably more than 80% by weight, of organosilanes of the formula I with —$S_2$— units.

Preferably, mixtures of organosilanes of the formula I may contain 50 to 100% by weight, preferably 60 to 95% by weight, more preferably 70 to 95% by weight, most preferably 75 to 90% by weight, of organosilanes of the formula I with —$S_2$— units.

Mixtures of organosilanes of the formula I may contain less than 60% by weight, preferably less than 45% by weight, more preferably less than 35% by weight, most preferably less than 25% by weight, of organosilanes of the formula I with —$S_3$— units.

Preferably, mixtures of organosilanes of the formula I may contain up to 60% by weight, preferably 5 to 45% by weight, more preferably 8 to 35% by weight, most preferably 10 to 25% by weight, of organosilanes of the formula I with —$S_3$— units.

Mixtures of organosilanes of the formula I may contain less than 50% by weight, preferably less than 30% by weight, more preferably less than 20% by weight, most preferably less than 10% by weight, of organosilanes of the formula I with —$S_4$— units.

The compounds of the general formula I formed in the process according to the invention or the mixtures of compounds of the general formula I may have a water content of less than 2% by weight, preferably less than 1% by weight, more preferably less than 0.5% by weight, most preferably less than 0.1% by weight. The water content is measured to DIN ENISO 12937 including an iodometric back-titration in order to be able to distinguish $H_2O$ and HS species ($H_2S$, etc.).

The alkyl polyether group (R') in formula I and II may contain ethylene oxide ($CH_2$—$CH_2$—O) and propylene oxide units, for example ($CH(CH_3)$—$CH_2$—O) or ($CH_2$—$CH(CH_3)$—O).

The alkyl polyether group —$(CR^{III}_2O)_y$-Alk or O—$(CR^{III}_2$—$CR^{III}_2O)_y$-Alk in formula I and II may be
—($CH_2$—$CH_2O)_2$—$C_8H_{17}$, —($CH_2$—$CH_2O)_3$—$C_8H_{17}$, —($CH_2$—$CH_2O)_4$—$C_8H_{17}$, —($CH_2$—$CH_2O)_5$—$C_8H_{17}$, —($CH_2$—$CH_2O)_6$—$C_8H_{17}$, —($CH_2$—$CH_2O)_7$—$C_8H_{17}$,
—($CH(CH_3)$—$CH_2O)_2$—$C_8H_{17}$, —($CH(CH_3)$—$CH_2O)_3$—$C_8H_{17}$, —($CH(CH_3)$—$CH_2O)_4$—$C_8H_{17}$, —($CH(CH_3)$—$CH_2O)_5$—$C_8H_{17}$, —($CH(CH_3)$—$CH_2O)_6$—$C_8H_{17}$, —($CH(CH_3)$—$CH_2O)_7$—$C_8H_{17}$,
($CH_2$—$CH_2O)_2$—$C_9H_{19}$, —($CH_2$—$CH_2O)_3$—$C_9H_{19}$, —($CH_2$—$CH_2O)_4$—$C_9H_{19}$, —($CH_2$—$CH_2O)_5$—$C_9H_{19}$, —($CH_2$—$CH_2O)_6$—$C_9H_{19}$, —($CH_2$—$CH_2O)_7$—$C_9H_{19}$,
—($CH(CH_3)$—$CH_2O)_2$—$C_9H_{19}$, —($CH(CH_3)$—$CH_2O)_3$—$C_9H_{19}$, —($CH(CH_3)$—$CH_2O)_4$—$C_9H_{19}$, —($CH(CH_3)$—$CH_2O)_5$—$C_9H_{19}$, —($CH(CH_3)$—$CH_2O)_6$—$C_9H_{19}$, —($CH(CH_3)$—$CH_2O)_7$—$C_9H_{19}$,
—($CH_2$—$CH_2O)_2$—$C_{10}H_{21}$, —($CH_2$—$CH_2O)_3$—$C_{10}H_{21}$, —($CH_2$—$CH_2O)_4$—$C_{10}H_{21}$, —($CH_2$—$CH_2O)_5$—$C_{10}H_{21}$, —($CH_2$—$CH_2O)_6$—$C_{10}H_{21}$, —($CH_2$—$CH_2O)_7$—$C_{10}H_{21}$,
—($CH(CH_3)$—$CH_2O)_2$—$C_{10}H_{21}$, —($CH(CH_3)$—$CH_2O)_3$—$C_{10}H_{21}$, —($CH(CH_3)$—$CH_2O)_4$—$C_{10}H_{21}$, —($CH(CH_3)$—$CH_2O)_5$—$C_{10}H_{21}$, —($CH(CH_3)$—$CH_2O)_6$—$C_{10}H_{21}$, —($CH(CH_3)$—$CH_2O)_7$—$C_{10}H_{21}$,
($CH_2$—$CH_2O)_2$—$C_{11}H_{23}$, —($CH_2$—$CH_2O)_3$—$C_{11}H_{23}$, —($CH_2$—$CH_2O)_4$—$C_{11}H_{23}$, —($CH_2$—$CH_2O)_5$—$C_{11}H_{23}$, —($CH_2$—$CH_2O)_6$—$C_{11}H_{23}$, —($CH_2$—$CH_2O)_7$—$C_{11}H_{23}$,
—($CH(CH_3)$—$CH_2O)_2$—$C_{11}H_{23}$, —($CH(CH_3)$—$CH_2O)_3$—$C_{11}H_{23}$, —($CH(CH_3)$—$CH_2O)_4$—$C_{11}H_{23}$, —($CH(CH_3)$—$CH_2O)_5$—$C_{11}H_{23}$, —($CH(CH_3)$—$CH_2O)_6$—$C_{11}H_{23}$, —($CH(CH_3)$—$CH_2O)_7$—$C_{11}H_{23}$,
—($CH_2$—$CH_2O)_2$—$C_{12}H_{25}$, —($CH_2$—$CH_2O)_3$—$C_{12}H_{25}$, —($CH_2$—$CH_2O)_4$—$C_{12}H_{25}$, —($CH_2$—$CH_2O)_5$—$C_{12}H_{25}$, —($CH_2$—$CH_2O)_6$—$C_{12}H_{25}$, —($CH_2$—$CH_2O)_7$—$C_{12}H_{25}$,
—($CH(CH_3)$—$CH_2O)_2$—$C_{12}H_{25}$, —($CH(CH_3)$—$CH_2O)_3$—$C_{12}H_{25}$, —($CH(CH_3)$—$CH_2O)_4$—$C_{12}H_{25}$, —($CH(CH_3)$—$CH_2O)_5$—$C_{12}H_{25}$, —($CH(CH_3)$—$CH_2O)_6$—$C_{12}H_{25}$, —($CH(CH_3)$—$CH_2O)_7$—$C_{12}H_{25}$,
—($CH_2$—$CH_2O)_2$—$C_{13}H_{27}$, —($CH_2$—$CH_2O)_3$—$C_{13}H_{27}$, —($CH_2$—$CH_2O)_4$—$C_{13}H_{27}$, —($CH_2$—$CH_2O)_5$—$C_{13}H_{27}$, —($CH_2$—$CH_2O)_6$—$C_{13}H_{27}$, —($CH_2$—$CH_2O)_7$—$C_{13}H_{27}$,
—($CH(CH_3)$—$CH_2O)_2$—$C_{13}H_{27}$, —($CH(CH_3)$—$CH_2O)_3$—$C_{13}H_{27}$, —($CH(CH_3)$—$CH_2O)_4$—$C_{13}H_{27}$, —($CH(CH_3)$—$CH_2O)_5$—$C_{13}H_{27}$, —($CH(CH_3)$—$CH_2O)_6$—$C_{13}H_{27}$, —($CH(CH_3)$—$CH_2O)_7$—$C_{13}H_{27}$,
—($CH_2$—$CH_2O)_2$—$C_{14}H_{29}$, —($CH_2$—$CH_2O)_3$—$C_{14}H_{29}$, —($CH_2$—$CH_2O)_4$—$C_{14}H_{29}$, —($CH_2$—$CH_2O)_5$—$C_{14}H_{29}$, —($CH_2$—$CH_2O)_6$—$C_{14}H_{29}$, —($CH_2$—$CH_2O)_7$—$C_{14}H_{29}$,
—($CH(CH_3)$—$CH_2O)_2$—$C_{14}H_{29}$, —($CH(CH_3)$—$CH_2O)_3$—$C_{14}H_{29}$, —($CH(CH_3)$—$CH_2O)_4$—$C_{14}H_{29}$, —($CH(CH_3)$—$CH_2O)_5$—$C_{14}H_{29}$, —($CH(CH_3)$—$CH_2O)_6$—$C_{14}H_{29}$, —($CH(CH_3)$—$CH_2O)_7$—$C_{14}H_{29}$,
—($CH_2$—$CH_2O)_2$—$C_{15}H_{31}$, —($CH_2$—$CH_2O)_3$—$C_{15}H_{31}$, —($CH_2$—$CH_2O)_4$—$C_{15}H_{31}$, —($CH_2$—$CH_2O)_5$—$C_{15}H_{31}$, —($CH_2$—$CH_2O)_6$—$C_{15}H_{31}$, —($CH_2$—$CH_2O)_7$—$C_{15}H_{31}$,
—($CH(CH_3)$—$CH_2O)_2$—$C_{15}H_{31}$, —($CH(CH_3)$—$CH_2O)_3$—$C_{15}H_{31}$, —($CH(CH_3)$—$CH_2O)_4$—$C_{15}H_{31}$, —($CH(CH_3)$—$CH_2O)_5$—$C_{15}H_{31}$, —($CH(CH_3)$—$CH_2O)_6$—$C_{15}H_{31}$, —($CH(CH_3)$—$CH_2O)_7$—$C_{15}H_{31}$,
—($CH_2$—$CH_2O)_2$—$C_{16}H_{33}$, —($CH_2$—$CH_2O)_3$—$C_{16}H_{33}$, —($CH_2$—$CH_2O)_4$—$C_{16}H_{33}$, —($CH_2$—$CH_2O)_5$—$C_{16}H_{33}$, —($CH_2$—$CH_2O)_6$—$C_{16}H_{33}$, —($CH_2$—$CH_2O)_7$—$C_{16}H_{33}$,
($CH(CH_3)$—$CH_2O)_2$—$C_{16}H_{33}$, —($CH(CH_3)$—$CH_2O)_3$—$C_{16}H_{33}$, —($CH(CH_3)$—$CH_2O)_4$—$C_{16}H_{33}$, —($CH(CH_3)$—$CH_2O)_5$—$C_{16}H_{33}$, —($CH(CH_3)$—$CH_2O)_6$—$C_{16}H_{33}$ or —($CH(CH_3)$—$CH_2O)_7$—$C_{16}H_{33}$.

Organosilanes of the general formula I may be:
[(MeO)$_3$Si(CH$_2$)$_3$]$_2$S$_m$, [(EtO)$_3$Si(CH$_2$)$_3$]$_2$S$_m$, [(C$_3$H$_7$O)$_3$Si(CH$_2$)$_3$]$_2$S$_m$, [(C$_{12}$H$_{25}$O)$_3$Si(CH$_2$)$_3$]S$_m$[(CH$_2$)$_3$Si(C$_{12}$H$_{25}$O)$_3$], [(C$_{14}$H$_{29}$O)$_3$Si(CH$_2$)$_3$]S$_m$[(CH$_2$)$_3$Si(C$_{14}$H$_{29}$O)$_3$], [(C$_{16}$H$_{33}$O)$_3$Si(CH$_2$)$_3$]S$_m$[(CH$_2$)$_3$Si(C$_{16}$H$_{33}$O)$_3$], [(C$_{18}$H$_{37}$O)$_3$Si(CH$_2$)$_3$]S$_m$[(CH$_2$)$_3$Si(C$_{18}$H$_{37}$O)$_3$],
[(C$_{12}$H$_{25}$O)$_2$(CH$_3$)Si(CH$_2$)$_3$]S$_m$[(CH$_2$)$_3$Si(CH$_3$)(C$_{12}$H$_{2}$O)$_2$], [(C$_{12}$H$_{25}$O)(C$_{14}$H$_{29}$O)(CH$_3$)Si(CH$_2$)$_3$]S$_m$[(CH$_2$)$_3$Si(CH$_3$)(C$_{12}$H$_{25}$O)(C$_{14}$H$_{29}$O)], [(C$_{12}$H$_{25}$O)(C$_{14}$H$_{21}$O)(CH$_3$)Si(CH$_2$)$_3$]S$_m$[(CH$_2$)$_3$Si(CH$_3$)(C$_{12}$H$_{25}$O)(C$_{12}$H$_{25}$O)],
[(C$_{12}$H$_{25}$O)(C$_{16}$H$_{33}$O)(CH$_3$)Si(CH$_2$)$_3$]S$_m$[(CH$_2$)$_3$Si(CH$_3$)(C$_{12}$H$_{25}$O)(C$_{16}$H$_{33}$O)], [(C$_{12}$H$_{25}$O)(C$_{18}$H$_{37}$O)(CH$_3$)Si(CH$_2$)$_3$]S$_m$[(CH$_2$)$_3$Si(CH$_3$)(C$_{12}$H$_{25}$O)(C$_{18}$H$_{37}$O)],
[(C$_{14}$H$_{29}$O)$_2$(CH$_3$)Si(CH$_2$)$_3$]S$_m$[(CH$_2$)$_3$Si(CH$_3$)(C$_{14}$H$_{29}$O)$_2$], [(C$_{14}$H$_{29}$O)(C$_{16}$H$_{33}$O)(CH$_3$)Si(CH$_2$)$_3$]S$_m$[(CH$_2$)$_3$Si(CH$_3$)(C$_{14}$H$_{29}$O)(C$_{16}$H$_{33}$O)], [(C$_{14}$H$_{29}$O)(C$_{18}$H$_{37}$O)(CH$_3$)Si(CH$_2$)$_3$]S$_m$[(CH$_2$)$_3$Si(CH$_3$)(C$_{14}$H$_{29}$O)(C$_{18}$H$_{37}$O)],
[(C$_{16}$H$_{33}$O)$_2$(CH$_3$)Si(CH$_2$)$_3$]S$_m$[(CH$_2$)$_3$Si(CH$_3$)(C$_{16}$H$_{33}$O)$_2$], [(C$_{16}$H$_{33}$O)(C$_{18}$H$_{37}$O)(CH$_3$)Si(CH$_2$)$_3$]S$_m$[(CH$_2$)$_3$Si(CH$_3$)(C$_{16}$H$_{33}$O)(C$_{18}$H$_{37}$O)], [(C$_{18}$H$_{37}$O)$_2$(CH$_3$)Si(CH$_2$)$_3$]S$_m$[(CH$_2$)$_3$Si(CH$_3$)(C$_{18}$H$_{37}$O)$_2$], [(C$_{12}$H$_{25}$O)(CH$_3$)$_2$Si(CH$_2$)$_3$]S$_m$[(CH$_2$)$_3$Si(CH$_3$)$_2$(C$_{12}$H$_{25}$O)], [(C$_{12}$H$_{25}$O)(CH$_3$)$_2$Si(CH$_2$)$_3$]S$_m$[(CH$_2$)$_3$Si(CH$_3$)$_2$(C$_{14}$H$_{29}$O)], [(C$_{12}$H$_{25}$O)(CH$_3$)$_2$Si(CH$_2$)$_3$]S$_m$[(CH$_2$)$_3$Si(CH$_3$)$_2$(C$_{16}$H$_{33}$O)],
[(C$_{12}$H$_{25}$O)(CH$_3$)$_2$Si(CH$_2$)$_3$]S$_m$[(CH$_2$)$_3$Si(CH$_3$)$_2$(C$_{18}$H$_{37}$O)], [(C$_{14}$H$_{29}$O)(CH$_3$)$_2$Si(CH$_2$)$_3$]S$_m$[(CH$_2$)$_3$Si(CH$_3$)$_2$(C$_{14}$H$_{29}$O)], [(C$_{14}$H$_{29}$O)(CH$_3$)$_2$Si(CH$_2$)$_3$]S$_m$[(CH$_2$)$_3$Si(CH$_3$)$_2$(C$_{16}$H$_{33}$O)], [(C$_{14}$H$_{29}$O)(CH$_3$)$_2$Si(CH$_2$)$_3$]S$_m$

[(CH$_2$)$_3$Si(CH$_3$)$_2$(C$_{18}$H$_{37}$O)], [(C$_{16}$H$_{33}$O)(CH$_3$)$_2$Si(CH$_2$)$_3$]S$_m$[(CH$_2$)$_3$Si(CH$_3$)$_2$(C$_{16}$H$_{33}$O)], [(C$_{16}$H$_{33}$O)(CH$_3$)$_2$Si(CH$_2$)$_3$]S$_m$[(CH$_2$)$_3$Si(CH$_3$)$_2$(C$_{18}$H$_{37}$O)], [(C$_{18}$H$_{37}$O)(CH$_3$)$_2$Si(CH$_2$)$_3$]S$_m$[(CH$_2$)$_3$Si(CH$_3$)$_2$(C$_{18}$H$_{37}$O)], where m=1.5-4.5.

Specific examples of compounds which may be part of mixtures of the formula I may be:

[(MeO)$_3$Si(CH$_2$)$_3$]$_2$S, [(MeO)$_3$Si(CH$_2$)$_3$]$_2$S$_2$, [(MeO)$_3$Si(CH$_2$)$_3$]$_2$S$_3$, [(MeO)$_3$Si(CH$_2$)$_3$]$_2$S$_4$, [(MeO)$_3$Si(CH$_2$)$_3$]$_2$S$_5$, [(MeO)$_3$Si(CH$_2$)$_3$]$_2$S$_6$, [(MeO)$_3$Si(CH$_2$)$_3$]$_2$S$_7$, [(MeO)$_3$Si(CH$_2$)$_3$]$_2$S$_8$, [(MeO)$_3$Si(CH$_2$)$_3$]$_2$S$_9$, [(MeO)$_3$Si(CH$_2$)$_3$]$_2$S$_{10}$, [(MeO)$_3$Si(CH$_2$)$_3$]$_2$S$_{11}$, [(MeO)$_3$Si(CH$_2$)$_3$]$_2$S$_{12}$,

[(EtO)$_3$Si(CH$_2$)$_3$]$_2$S, [(EtO)$_3$Si(CH$_2$)$_3$]$_2$S$_2$, [(EtO)$_3$Si(CH$_2$)$_3$]$_2$S$_3$, [(EtO)$_3$Si(CH$_2$)$_3$]$_2$S$_4$, [(EtO)$_3$Si(CH$_2$)$_3$]$_2$S$_5$, [(EtO)$_3$Si(CH$_2$)$_3$]$_2$S$_6$, [(EtO)$_3$Si(CH$_2$)$_3$]$_2$S$_7$, [(EtO)$_3$Si(CH$_2$)$_3$]$_2$S$_8$, [(EtO)$_3$Si(CH$_2$)$_3$]$_2$S$_9$, [(EtO)$_3$Si(CH$_2$)$_3$]$_2$S$_{10}$, [(EtO)$_3$Si(CH$_2$)$_3$]$_2$S$_{11}$, [(EtO)$_3$Si(CH$_2$)$_3$]$_2$S$_{12}$,

[(C$_3$H$_7$O)$_3$Si(CH$_2$)$_3$]$_2$S, [(C$_3$H$_7$O)$_3$Si(CH$_2$)$_3$]$_2$S$_2$, [(C$_3$H$_7$O)$_3$Si(CH$_2$)$_3$]$_2$S$_3$, [(C$_3$H$_7$O)$_3$Si(CH$_2$)$_3$]$_2$S$_4$, [(C$_3$H$_7$O)$_3$Si(CH$_2$)$_3$]$_2$S$_5$, [(C$_3$H$_7$O)$_3$Si(CH$_2$)$_3$]$_2$S$_6$, [(C$_3$H$_7$O)$_3$Si(CH$_2$)$_3$]$_2$S$_7$, [(C$_3$H$_7$O)$_3$Si(CH$_2$)$_3$]$_2$S$_8$, [(C$_3$H$_7$O)$_3$Si(CH$_2$)$_3$]$_2$S$_9$, [(C$_3$H$_7$O)$_3$Si(CH$_2$)$_3$]$_2$S$_{10}$, [(C$_3$H$_7$O)$_3$Si(CH$_2$)$_3$]$_2$S$_{11}$, [(C$_3$H$_7$O)$_3$Si(CH$_2$)$_3$]$_2$S$_{12}$.

The (haloorganyl)alkoxysilanes of the formula II used may preferably be 3-chlorobutyl(triethoxysilane), 3-chlorobutyl(trimethoxysilane), 3-chlorobutyl(diethoxymethoxysilane), 3-chloropropyl(triethoxysilane), 3-chloropropyl(trimethoxysilane), 3-chloropropyl(diethoxymethoxysilane), 2-chloroethyl(triethoxysilane), 2-chloroethyl(trimethoxysilane), 2-chloroethyl(diethoxymethoxysilane), 1-chloromethyl(triethoxysilane), 1-chloromethyl(trimethoxysilane), 1-chloromethyl(diethoxymethoxysilane), 3-chloropropyl(diethoxymethylsilane), 3-chloropropyl(dimethoxymethylsilane), 2-chloroethyl(diethoxymethylsilane), 2-chloroethyl(dimethoxymethylsilane), 1-chloromethyl(diethoxymethylsilane), 1-chloromethyl(dimethoxymethylsilane), 3-chloropropyl(ethoxydimethylsilane), 3-chloropropyl(methoxydimethylsilane), 2-chloroethyl(ethoxydimethylsilane), 2-chloroethyl(methoxydimethylsilane), 1-chloromethyl(ethoxydimethylsilane), 1-chloromethyl(methoxydimethylsilane),

[(C$_9$H$_{19}$O—(CH$_2$—CH$_2$O)$_2$](MeO)$_2$Si(CH$_2$)$_3$Cl,
[(C$_9$H$_{19}$O—(CH$_2$—CH$_2$O)$_3$](MeO)$_2$Si(CH$_2$)$_3$Cl,
[(C$_9$H$_{19}$O—(CH$_2$—CH$_2$O)$_4$](MeO)$_2$Si(CH$_2$)$_3$Cl,
[(C$_9$H$_{19}$O—(CH$_2$—CH$_2$O)$_5$](MeO)$_2$Si(CH$_2$)$_3$Cl,
[(C$_8$H$_{19}$O—(CH$_2$—CH$_2$O)$_6$](MeO)$_2$Si(CH$_2$)$_3$Cl,
[(C$_{12}$H$_{25}$O—(CH$_2$—CH$_2$O)$_2$](MeO)$_2$Si(CH$_2$)$_3$Cl,
[(C$_{12}$H$_{25}$O—(CH$_2$—CH$_2$O)$_3$](MeO)$_2$Si(CH$_2$)$_3$Cl,
[(C$_{12}$H$_{25}$O—(CH$_2$—CH$_2$O)$_4$](MeO)$_2$Si(CH$_2$)$_3$Cl,
[(C$_{12}$H$_{25}$O—(CH$_2$—CH$_2$O)$_5$](MeO)$_2$Si(CH$_2$)$_3$Cl,
[(C$_{12}$H$_{25}$O—(CH$_2$—CH$_2$O)$_6$](MeO)$_2$Si(CH$_2$)$_3$Cl,
[(C$_{13}$H$_{27}$O—(CH$_2$—CH$_2$O)$_2$](MeO)$_2$Si(CH$_2$)$_3$Cl,
[(C$_{13}$H$_{27}$O—(CH$_2$—CH$_2$O)$_3$](MeO)$_2$Si(CH$_2$)$_3$Cl,
[(C$_{13}$H$_{27}$O—(CH$_2$—CH$_2$O)$_4$](MeO)$_2$Si(CH$_2$)$_3$Cl,
[(C$_{13}$H$_{27}$O—(CH$_2$—CH$_2$O)$_5$](MeO)$_2$Si(CH$_2$)$_3$Cl,
[(C$_{13}$H$_{27}$O—(CH$_2$—CH$_2$O)$_6$](MeO)$_2$Si(CH$_2$)$_3$Cl,
[(C$_{14}$H$_{29}$O—(CH$_2$—CH$_2$O)$_2$](MeO)$_2$Si(CH$_2$)$_3$Cl,
[(C$_{14}$H$_{29}$O—(CH$_2$—CH$_2$O)$_3$](MeO)$_2$Si(CH$_2$)$_3$Cl,
[(C$_{14}$H$_{29}$O—(CH$_2$—CH$_2$O)$_4$](MeO)$_2$Si(CH$_2$)$_3$Cl,
[(C$_{14}$H$_{29}$O—(CH$_2$—CH$_2$O)$_5$](MeO)$_2$Si(CH$_2$)$_3$Cl,
[(C$_{14}$H$_{29}$O—(CH$_2$—CH$_2$O)$_6$](MeO)$_2$Si(CH$_2$)$_3$Cl,
[(C$_9$H$_{19}$O—(CH$_2$—CH$_2$O)$_2$]$_2$(MeO)Si(CH$_2$)$_3$Cl,
[(C$_9$H$_{19}$O—(CH$_2$—CH$_2$O)$_3$]$_2$(MeO)Si(CH$_2$)$_3$Cl,
[(C$_9$H$_{19}$O—(CH$_2$—CH$_2$O)$_4$]$_2$(MeO)Si(CH$_2$)$_3$Cl,
[(C$_9$H$_{19}$O—(CH$_2$—CH$_2$O)$_5$]$_2$(MeO)Si(CH$_2$)$_3$Cl,
[(C$_9$H$_{19}$O—(CH$_2$—CH$_2$O)$_6$]$_2$(MeO)Si(CH$_2$)$_3$Cl,
[(C$_{12}$H$_{25}$O—(CH$_2$—CH$_2$O)$_2$]$_2$(MeO)Si(CH$_2$)$_3$Cl,
[(C$_{12}$H$_{25}$O—(CH$_2$—CH$_2$O)$_3$]$_2$(MeO)Si(CH$_2$)$_3$Cl,
[(C$_{12}$H$_{25}$O—(CH$_2$—CH$_2$O)$_4$]$_2$(MeO)Si(CH$_2$)$_3$Cl,
[(C$_{12}$H$_{25}$O—(CH$_2$—CH$_2$O)$_5$]$_2$(MeO)Si(CH$_2$)$_3$Cl,
[(C$_{12}$H$_{25}$O—(CH$_2$—CH$_2$O)$_6$]$_2$(MeO)Si(CH$_2$)$_3$Cl,
[(C$_{13}$H$_{27}$O—(CH$_2$—CH$_2$O)$_2$]$_2$(MeO)Si(CH$_2$)$_3$Cl,
[(C$_{13}$H$_{27}$O—(CH$_2$—CH$_2$O)$_3$]$_2$(MeO)Si(CH$_2$)$_3$Cl,
[(C$_{13}$H$_{27}$O—(CH$_2$—CH$_2$O)$_4$]$_2$(MeO)Si(CH$_2$)$_3$Cl,
[(C$_{13}$H$_{27}$O—(CH$_2$—CH$_2$O)$_5$]$_2$(MeO)Si(CH$_2$)$_3$Cl,
[(C$_{13}$H$_{27}$O—(CH$_2$—CH$_2$O)$_6$]$_2$(MeO)Si(CH$_2$)$_3$Cl,
[(C$_{14}$H$_{29}$O—(CH$_2$—CH$_2$O)$_2$]$_2$(MeO)Si(CH$_2$)$_3$Cl,
[(C$_{14}$H$_{29}$O—(CH$_2$—CH$_2$O)$_3$]$_2$(MeO)Si(CH$_2$)$_3$Cl,
[(C$_{14}$H$_{29}$O—(CH$_2$—CH$_2$O)$_4$]$_2$(MeO)Si(CH$_2$)$_3$Cl,
[(C$_{14}$H$_{29}$O—(CH$_2$—CH$_2$O)$_5$]$_2$(MeO)Si(CH$_2$)$_3$Cl,
[(C$_{14}$H$_{29}$O—(CH$_2$—CH$_2$O)$_6$]$_2$(MeO)Si(CH$_2$)$_3$Cl,
[(C$_9$H$_{19}$O—(CH$_2$—CH$_2$O)$_2$](EtO)$_2$Si(CH$_2$)$_3$Cl,
[(C$_9$H$_{19}$O—(CH$_2$—CH$_2$O)$_3$](EtO)$_2$Si(CH$_2$)$_3$Cl,
[(C$_9$H$_{19}$O—(CH$_2$—CH$_2$O)$_4$](EtO)$_2$Si(CH$_2$)$_3$Cl,
[(C$_9$H$_{19}$O—(CH$_2$—CH$_2$O)$_5$](EtO)$_2$Si(CH$_2$)$_3$Cl,
[(C$_9$H$_{19}$O—(CH$_2$—CH$_2$O)$_6$](EtO)$_2$Si(CH$_2$)$_3$Cl,
[(C$_{12}$H$_{25}$O—(CH$_2$—CH$_2$O)$_2$](EtO)$_2$Si(CH$_2$)$_3$Cl,
[(C$_{12}$H$_{25}$O—(CH$_2$—CH$_2$O)$_3$](EtO)$_2$Si(CH$_2$)$_3$Cl,
[(C$_{12}$H$_{25}$O—(CH$_2$—CH$_2$O)$_4$](EtO)$_2$Si(CH$_2$)$_3$Cl,
[(C$_{12}$H$_{25}$O—(CH$_2$—CH$_2$O)$_5$](EtO)$_2$Si(CH$_2$)$_3$Cl,
[(C$_{12}$H$_{25}$O—(CH$_2$—CH$_2$O)$_6$](EtO)$_2$Si(CH$_2$)$_3$Cl,
[(C$_{13}$H$_{27}$O—(CH$_2$—CH$_2$O)$_2$](EtO)$_2$Si(CH$_2$)$_3$Cl,
[(C$_{13}$H$_{27}$O—(CH$_2$—CH$_2$O)$_3$](EtO)$_2$Si(CH$_2$)$_3$Cl,
[(C$_{13}$H$_{27}$O—(CH$_2$—CH$_2$O)$_4$](EtO)$_2$Si(CH$_2$)$_3$Cl,
[(C$_{13}$H$_{27}$O—(CH$_2$—CH$_2$O)$_5$](EtO)$_2$Si(CH$_2$)$_3$Cl,
[(C$_{13}$H$_{27}$O—(CH$_2$—CH$_2$O)$_6$](EtO)$_2$Si(CH$_2$)$_3$Cl,
[(C$_{14}$H$_{29}$O—(CH$_2$—CH$_2$O)$_2$](EtO)$_2$Si(CH$_2$)$_3$Cl,
[(C$_{14}$H$_{29}$O—(CH$_2$—CH$_2$O)$_3$](EtO)$_2$Si(CH$_2$)$_3$Cl,
[(C$_{14}$H$_{29}$O—(CH$_2$—CH$_2$O)$_4$](EtO)$_2$Si(CH$_2$)$_3$Cl,
[(C$_{14}$H$_{29}$O—(CH$_2$—CH$_2$O)$_5$](EtO)$_2$Si(CH$_2$)$_3$Cl,
[(C$_{14}$H$_{29}$O—(CH$_2$—CH$_2$O)$_6$](EtO)$_2$Si(CH$_2$)$_3$Cl,
[(C$_9$H$_{19}$O—(CH$_2$—CH$_2$O)$_2$]$_2$(EtO)Si(CH$_2$)$_3$Cl,
[(C$_9$H$_{19}$O—(CH$_2$—CH$_2$O)$_3$]$_2$(EtO)Si(CH$_2$)$_3$Cl,
[(C$_9$H$_{19}$O—(CH$_2$—CH$_2$O)$_4$]$_2$(EtO)Si(CH$_2$)$_3$Cl,
[(C$_9$H$_{19}$O—(CH$_2$—CH$_2$O)$_5$]$_2$(EtO)Si(CH$_2$)$_3$Cl,
[(C$_9$H$_{19}$O—(CH$_2$—CH$_2$O)$_6$]$_2$(EtO)Si(CH$_2$)$_3$Cl,
[(C$_{12}$H$_{25}$O—(CH$_2$—CH$_2$O)$_2$]$_2$(EtO)Si(CH$_2$)$_3$Cl,
[(C$_{12}$H$_{25}$O—(CH$_2$—CH$_2$O)$_3$]$_2$(EtO)Si(CH$_2$)$_3$Cl,
[(C$_{12}$H$_{25}$O—(CH$_2$—CH$_2$O)$_4$]$_2$(EtO)Si(CH$_2$)$_3$Cl,
[(C$_{12}$H$_{25}$O—(CH$_2$—CH$_2$O)$_5$]$_2$(EtO)Si(CH$_2$)$_3$Cl,
[(C$_{12}$H$_{25}$O—(CH$_2$—CH$_2$O)$_6$]$_2$(EtO)Si(CH$_2$)$_3$Cl,
[(C$_{13}$H$_{27}$O—(CH$_2$—CH$_2$O)$_2$]$_2$(EtO)Si(CH$_2$)$_3$Cl,
[(C$_{13}$H$_{27}$O—(CH$_2$—CH$_2$O)$_3$]$_2$(EtO)Si(CH$_2$)$_3$Cl,
[(C$_{13}$H$_{27}$O—(CH$_2$—CH$_2$O)$_4$]$_2$(EtO)Si(CH$_2$)$_3$Cl,
[(C$_{13}$H$_{27}$O—(CH$_2$—CH$_2$O)$_5$]$_2$(EtO)Si(CH$_2$)$_3$Cl,
[(C$_{13}$H$_{27}$O—(CH$_2$—CH$_2$O)$_6$]$_2$(EtO)Si(CH$_2$)$_3$Cl,
[(C$_{14}$H$_{29}$O—(CH$_2$—CH$_2$O)$_2$]$_2$(EtO)Si(CH$_2$)$_3$Cl,
[(C$_{14}$H$_{29}$O—(CH$_2$—CH$_2$O)$_3$]$_2$(EtO)Si(CH$_2$)$_3$Cl,
[(C$_{14}$H$_{29}$O—(CH$_2$—CH$_2$O)$_4$]$_2$(EtO)Si(CH$_2$)$_3$Cl,
[(C$_{14}$H$_{29}$O—(CH$_2$—CH$_2$O)$_5$]$_2$(EtO)Si(CH$_2$)$_3$Cl,
[(C$_{14}$H$_{29}$O—(CH$_2$—CH$_2$O)$_6$]$_2$(EtO)Si(CH$_2$)$_3$Cl,
[(C$_9$H$_{19}$O—(CH$_2$—CH$_2$O)$_2$]$_3$Si(CH$_2$)$_3$Cl, [(C$_9$H$_{19}$O—(CH$_2$—CH$_2$O)$_3$]$_3$Si(CH$_2$)$_3$Cl, [(C$_9$H$_{19}$O—(CH$_2$—CH$_2$O)$_4$]$_3$Si(CH$_2$)$_3$Cl, [(C$_9$H$_{19}$O—(CH$_2$—CH$_2$O)$_6$]$_3$Si(CH$_2$)$_3$Cl, [(C$_9$H$_{19}$O—(CH$_2$—CH$_2$O)$_6$]$_3$Si(CH$_2$)$_3$Cl,
[(C$_{12}$H$_{25}$O—(CH$_2$—CH$_2$O)$_2$]$_3$Si(CH$_2$)$_3$Cl, [(C$_{12}$H$_{25}$O—(CH$_2$—CH$_2$O)$_3$]$_3$Si(CH$_2$)$_3$Cl, [(C$_{12}$H$_{25}$O—(CH$_2$—CH$_2$O)$_4$]$_3$Si(CH$_2$)$_3$Cl, [(C$_{12}$H$_{25}$O—(CH$_2$—CH$_2$O)$_5$]$_3$Si(CH$_2$)$_3$Cl, [(C$_{12}$H$_{25}$O—(CH$_2$—CH$_2$O)$_2$]$_3$Si(CH$_2$)$_3$Cl,

[(C₁₃H₂₇O—(CH₂—CH₂O)₂]₃Si(CH₂)₃Cl, [(C₁₃H₂₇O—(CH₂—CH₂O)₃]₃Si(CH₂)₃Cl, [(C₁₃H₂₇O—(CH₂—CH₂O)₄]₃Si(CH₂)₃Cl, [(C₁₃H₂₇O—(CH₂—CH₂O)₅]₃Si(CH₂)₃Cl, [(C₁₃H₂₇O—(CH₂—CH₂O)₆]₃Si(CH₂)₃Cl,

[(C₁₄H₂₉O—(CH₂—CH₂O)₂]₃Si(CH₂)₃Cl, [(C₁₄H₂₉O—(CH₂—CH₂O)₃]₃Si(CH₂)₃Cl, [(C₁₄H₂₉O—(CH₂—CH₂O)₄]₃Si(CH₂)₃Cl, [(C₁₄H₂₉O—(CH₂—CH₂O)₅]₃Si(CH₂)₃Cl or [(C₁₄H₂₉O—(CH₂—CH₂O)₆]₃Si(CH₂)₃Cl.

The (haloorganyl)alkoxysilane may be a (haloorganyl)alkoxysilane of the formula II or a mixture of (haloorganyl)alkoxysilanes of the formula II.

Alkali metal hydrogensulphide may be NaSH, LiSH, KSH or CsSH. The alkali metal hydrogensulphide may be a purified form or a form comprising secondary constituents.

Preferably, sodium hydrogensulphide can be used.

The alkali metal hydrogensulphide may be used in solid form.

The hydrous solid alkali metal hydrogensulphide may contain between 1 and 80% by weight, preferably between 5 and 65% by weight, more preferably between 10 and 55% by weight and exceptionally preferably between 20 and 45% by weight of water.

The alkali metal hydrogensulphide may be present dissolved in water.

The alkali metal hydrogensulphide dissolved in water may contain more than 15% by weight, preferably more than 25% by weight, more preferably more than 35% by weight, even more preferably more than 45% by weight and exceptionally preferably more than 55% by weight of water.

The alkali metal hydrogensulphides used may be added to the reaction as solids or in solution.

The hydrous alkali metal hydrogensulphide and the sulphur can be added to the reaction together or independently as solids or in solution.

The hydrous alkali metal hydrogensulphide, the sulphur and the alkali metal carbonate can be added to the reaction together or independently as solids or in solution.

The alkali metal hydrogensulphide can be analysed in the following manner, detailed by way of example for NaSH hydrate:

approx. 3 g of sample (sodium hydrogensulphide) are weighed into a 100 ml standard flask (balance (readability 1 mg or better)) and dissolved in approx. 75 ml of ultrapure water.

Subsequently, 10 ml of barium chloride (10% barium chloride solution in ultrapure water) are added, and the mixture is shaken and made up to the mark.

After making it up to the mark, there is a wait of one hour until the precipitate formed has settled. 10 ml of the clear, supernatant solution are pipetted with a volumetric pipette into a 150 ml beaker and diluted with about 100 ml of ultrapure water. Subsequently, a dynamic pH titration with HCl c(HCl)=0.1 mol/l is carried out (pH electrode, titration system).

Here, the first changeover point between pH 9 and pH 10 corresponds to the NaOH content (in solution) according to the following reaction:

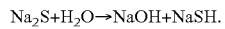

At the second changeover point between pH 4 and pH 5, the NaSH present in solution is converted according to the following equation:

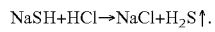

Calculation:

$$\text{NaOH}_{solution}[\% \text{ m/m}] = \frac{V_1 \times M_{NaOH} \times m_{HCl} \times F \times 100 \times V_{MK}}{E \times V_P}$$

$V_1$=first changeover point (ml)
$M_{NaOH}$=molar mass of NaOH (39.99 g/mol)
$m_{HCl}$=molarity of the hydrochloric acid solution
E=starting weight in mg
F=titre of hydrochloric acid
$V_P$=pipette volume (ml)
$V_{MK}$=standard flask volume (ml)

$$\text{NaSH}_{solution}[\% \text{ m/m}] = \frac{[V_2 - (V_1)] \times M_{NaSH} \times m_{HCl} \times F \times 100 \times V_{MK}}{E \times V_P}$$

$V_2$=second changeover point (ml)
$V_1$=first changeover point (ml)
$M_{NaSH}$=molar mass of NaSH (56.064 g/mol)
$m_{HCl}$=molarity of the hydrochloric acid solution
E=starting weight in mg
F=titre of hydrochloric acid
$V_P$=pipette volume (ml)
$V_{MK}$=standard flask volume (ml)

The alkali metal hydrogensulphide present in the solid raw material can be determined by means of the following equation:

$$\text{NaSH}_{solid}[\% \text{ m/m}] = \frac{[V_2 - (V_1 \times 2)] \times M_{NaSH} \times m_{HCl} \times F \times 100 \times V_{MK}}{E \times V_P}$$

The alkali metal hydrogensulphides may, as well as water, comprise further secondary constituents to an extent of less than 30% by weight, preferably less than 20% by weight, more preferably less than 10% by weight, most preferably less than 5% by weight.

Based on the amount of alkali metal hydrogensulphide in the alkali metal hydrogensulphide raw material used, it is possible for between 0 and 10% by weight, preferably between 0.4 and 8% by weight, more preferably between 0.6 and 5% by weight and most preferably between 0.8 and 3% by weight of alkali metal sulphide to be present therein.

Based on the amount of alkali metal hydrogensulphide in the alkali metal hydrogensulphide raw material used, it is possible for less than 10% by weight, preferably less than 8% by weight, more preferably less than 5% by weight and most preferably less than 3% by weight of alkali metal hydroxide to be present therein.

It is possible for more than 0.44% by weight of alkali metal hydroxide to be present in the dissolved alkali metal hydrogensulphide sulphurization raw material.

The process can be carried out without separate addition of alkali metal sulphide hydrate in solid or dissolved form.

Further secondary constituents of alkali metal hydrogensulphides may, as well as water, independently be alkali metal sulphates, alkali metal hydrogensulphates, alkali metal thiosulphates and/or alkali metal hydrogenthiosulphates.

The water content of the alkali metal hydrogensulphides is determined by Karl-Fischer titration analogously to DIN 51777. In this determination, the disruptive influences of sulphur-containing components are taken into account by an iodometric back-titration according to the known principles and methods.

Alkali metal carbonate may be $Na_2CO_3$, $Li_2CO_3$, $K_2CO_3$ or $Cs_2CO_3$. $Na_2CO_3$ may be preferred.

The process according to the invention can be implemented with virtually dust-free alkali metal carbonate and/or with finely divided alkali metal carbonate.

Virtually dust-free alkali metal carbonate may preferably have an average particle size (median) of >50 μm, preferably >100 μm, more preferably >200 μm, most preferably >300 μm, measured by laser diffraction analysis or screening.

Virtually dust-free alkali metal carbonate may have an average particle size (median) between 50 and 2000 μm, preferably between 100 and 1500 μm, more preferably between 150 and 1000 μm, most preferably between 200 and 500 μm, measured by laser diffraction analysis or screening.

Finely divided alkali metal carbonate may have an average particle size (median) of <500 μm, preferably <250 μm, more preferably <150 μm, most preferably <100 μm, measured by laser diffraction analysis or screening.

Finely divided alkali metal carbonate may have an average particle size (median) between 20 and 200 μm, preferably between 30 and 180 μm, more preferably between 40 and 150 μm, most preferably between 50 and 150 μm, measured by laser diffraction analysis or screening.

The particle size distribution of the samples is determined by laser diffraction analysis without ultrasound treatment with a Coulter LS 100 with a dry powder module (from Beckman-Coulter) according to the commonly known rules and operating methods. For 60 sec., a continuous stream of original, untreated particles of the sample to be analysed is conducted through a laser beam in an air jet. The beam passes through the particle stream and the different particle sizes are detected and evaluated statistically. The measurable particle size is not less than 0.4 μm and not more than 900 μm.

The particle size distribution by screening is determined as follows:

a particular amount of sample is separated with a stack of screens of different, standardized mesh size.

The proportion of the individual fractions is determined by weighing. The equipment used for this: mechanical screening machine (Ro-tap); precision balance: accuracy ±0.01 g (from Mettler).

Standard screens: U.S. standard No. 120, height 25 mm, Ø: 200 mm; mesh sizes, for example: 300 μm (50 mesh); 150 μm (100 mesh); 75 μm (200 mesh).

The screens and a collecting vessel are assembled in the sequence envisaged, i.e. with opening size decreasing from the top downward. 100 g of the sample to be analysed are weighed using an appropriate shovel. Preliminary selection of the material by pouring out or transferring by pouring should be avoided. After the weighed material has been transferred to the uppermost screen, a lid is placed on and the stack is placed into the screening machine such that a play of approx. 1.5 mm remains and the screens can thus rotate freely.

The screens are secured in the machine and then shaken for 5 min—with the shaker or tapper in operation. Thereafter, the screens are dismantled successively and the amount of material present in each is weighed accurately to 0.1 g. A double determination of each sample is carried out. In each case, the mean of the amount of material found in the individual screens and in the collecting vessel is reported in %. The median can be calculated from the values for the fractions.

The process according to the invention can be carried out with virtually dust-free sulphur and/or with finely divided sulphur.

The virtually dust-free sulphur may have an average particle size, measured by screening, of >200 μm, preferably >500 μm, more preferably >1000 μm, most preferably >2000 μm.

The virtually dust-free sulphur may have an average particle size, measured by screening, between 1 μm and 20 000 μm, preferably between 100 μm and 10 000 μm, more preferably between 200 μm and 5000 μm, most preferably between 500 μm and 2000 μm.

The finely divided sulphur may have an average particle size, measured by screening, between 1 μm and 200 μm, preferably between 10 μm and 150 μm, more preferably between 10 μm and 100 μm, most preferably between 10 μm and 75 μm.

The finely divided sulphur may have an average particle size, measured by screening, of <500 μm, preferably <250 μm, more preferably <100 μm, most preferably <80 μm.

The molar ratio of (haloorganyl)alkoxysilane of the formula II to sulphur may be less than 1:0.4, preferably less than 1:0.45, more preferably less than 1:0.5, even more preferably less than 1:0.55, exceptionally preferably less than 1:0.6.

The molar ratio of (haloorganyl)alkoxysilane of the formula II to sulphur may be between 1:0.4 and 1:1.5, preferably between 1:0.45 and 1:1.4, more preferably between 1:0.5 and 1:1.35, even more preferably between 1:0.55 and 1:1.3 and exceptionally preferably between 1:0.6 and 1:1.15.

The molar ratio of (haloorganyl)alkoxysilane of the formula II to alkali metal carbonate may be less than 1:0.25, preferably less than 1:0.45, more preferably less than 1:0.5, even more preferably less than 1:0.55, exceptionally preferably less than 1:0.6.

The molar ratio of alkali metal carbonate to (haloorganyl)alkoxysilane of the formula II may be between 1:0.1 and 1:2, preferably between 1:0.2 and 1:1.5, more preferably between 1:0.3 and 1:1.0, even more preferably between 1:0.4 and 1:0.8, exceptionally preferably between 1:0.45 and 1:0.7.

The molar ratio of sulphur to alkali metal hydrogensulphide may be less than 1:0.25, preferably less than 1:0.45, more preferably less than 1:0.7, even more preferably less than 1:0.9, exceptionally preferably less than 1:1.0.

The molar ratio of alkali metal hydrogensulphide to sulphur may be between 1:0.1 and 1:3, preferably between 1:0.3 and 1:2.75, more preferably between 1:0.5 and 1:2, even more preferably between 1:0.7 and 1:1.7, exceptionally preferably between 1:0.85 and 1:1.4.

The molar ratio of sulphur to alkali metal carbonate may be greater than 1:1.5, preferably greater than 1:1.4, more preferably greater than 1:1.3, even more preferably greater than 1:1.2, exceptionally preferably greater than 1:1.1, when m<2.5.

The molar ratio of alkali metal carbonate to sulphur may be less than 1:1.5, preferably less than 1:1.8, more preferably less than 1:2.0, even more preferably less than 1:2.3, exceptionally preferably less than 1:2.5, when m>2.5.

The molar ratio of alkali metal carbonate to sulphur may be between 1:0.1 and 1:3, preferably between 1:0.3 and 1:2.75, more preferably between 1:0.5 and 1:2, even more preferably between 1:0.7 and 1:1.55, exceptionally preferably between 1:0.85 and 1:1.4.

The process according to the invention can be carried out without a phase transfer catalyst. The process according to the invention can be carried out without tetraalkylammonium halide.

Additives may be added before, during or after the reaction.

Additives may be nonalcoholic solvents.

The additives used which are nonalcoholic solvents may preferably, in pure or technical-grade quality, be alkanes, for example pentane, hexane, cyclohexane, heptane or octane, ethers, for example diethyl ether, tetrahydrofuran, 1,2-dimethoxyethane, dioxane, dioxolane, ethylene glycols or propylene glycols, aromatic solvents, for example benzene, toluene, o-xylene, m-xylene or p-xylene, or carbonyl-containing solvents, for example dimethylformamide.

Before the reaction and/or during the reaction and/or toward the end of the reaction and/or during the workup, polar, protic, aprotic, basic or acidic additives can be added to the reaction mixture.

Additives may, for example, be organic or inorganic acids or organic or inorganic bases.

Inorganic acids may, for example, be compounds of the composition HCl, $H_2S$, $H_2SO_4$, $H_3PO_4$, (alkali metal)$H_2PO_4$, (alkali metal)$_2HPO_4$, $H_3CO_3$ or (alkali metal)$HSO_4$.

Inorganic bases may, for example, be compounds of the composition (alkali metal)$HCO_3$, (alkali metal)$_2HPO_4$ or (alkali metal)$_3PO_4$.

Acidic or basic additives which are added to the reaction mixture before, during or toward the end of the process may have the structure (alkali metal)$HCO_3$, (alkali metal)$H_2PO_4$, (alkali metal)$_2HPO_4$, (alkali metal)$_3PO_4$, (alkali metal)$_2SO_4$ or (alkali metal)$HSO_4$.

(Alkali metal)$HCO_3$ can preferably be added during or at the end of the process or during the workup.

The additives used may be (haloorganyl)halosilanes.

The (haloorganyl)halosilanes used may be compounds of the general formula III

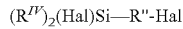

$$(R^{IV})_2(Hal)Si-R''-Hal \qquad III$$

where Hal, R and R″ are each as defined above and $R^{IV}$ is independently R or Hal.

The (haloorganyl)halosilanes used may preferably be (chloroorganyl)chlorosilanes.

The (haloorganyl)halosilane may be a (haloorganyl)halosilane of the general formula III or a mixture of (haloorganyl)chlorosilanes of the general formula III.

The amount of hydrolysable silicon halide in mixtures of (haloorganyl)alkyloxysilane and (haloorganyl)halosilane, which can be determined by the analysis method specified, may be between 2 and 800 000 mg/kg, preferably between 2 and 50 000 mg/kg, more preferably between 5 and 10 000 mg/kg, most preferably between 10 and 500 mg/kg.

The amount of hydrolysable halide in the mixtures of (haloorganyl)alkoxysilane and (haloorganyl)halosilane used is determined by the following method: not more than 20 g of the sample are admixed in a 150 ml beaker with 80 ml of ethanol and 10 ml of acetic acid. The halide content is titrated potentiographically with silver nitrate solution (c(AgNO$_3$)=0.01 mol/l).

The additives added before or/and during or/and at the end of the reaction may be compounds which, in conjunction with alcohols, release inorganic or organic acids.

The additives added before or/and during or/and at the end of the reaction may be compounds which, in conjunction with alcohols, release inorganic or organic bases.

The alcohol used may be primary, secondary or tertiary alcohols having 1 to 24, preferably 1 to 6 and more preferably 1 to 4 carbon atoms.

The alcohols used may be alkyl ethers of the formula HO—$(CR^V_2)_{y'}$—O-Alk where y' is as defined above, or alkyl polyethers of the formula HO—$(CR^V_2O)_y$-Alk or HO—$(CR^V_2$—$CR^V_2$—O)$_y$-Alk where y is as defined above, $R^V$ is independently H or an alkyl group, preferably $CH_3$ group, and Alk is as defined above.

The primary, secondary or tertiary alcohols used may be methanol, ethanol, n-propanol, i-propanol, i-butanol, n-butanol, dodecanol, tetradecanol, hexadecanol or octadecanol. The alkyl polyethers used may be HO—$(CH_2$—$CH_2$—O)$_a$—$C_bH_{2b+1}$, where a is 2 to 20, preferably 2-10, more preferably 2-8, most preferably 3-6, and b=1-30, preferably 2-20, more preferably 6-18, most preferably 10-18.

The alcohol used may preferably be ethanol.

Primary alcohols may be
HO—$(CH_2$—$CH_2$—O)$_2$—$C_6H_{13}$, HO—$(CH_2$—$CH_2$—O)$_3$—$C_6H_{13}$, HO—$(CH_2$—$CH_2$—O)$_4$—$C_6H_{13}$, HO—$(CH_2$—$CH_2$—O)$_5$—$C_6H_{13}$, HO—$(CH_2$—$CH_2$—O)$_6$—$C_6H_{13}$, HO—$(CH_2$—$CH_2$—O)$_7$—$C_6H_{13}$, HO—$(CH_2$—$CH_2$—O)$_8$—$C_6H_{13}$, HO—$(CH_2$—$CH_2$—O)$_9$—$C_6H_{13}$,
HO—$(CH_2$—$CH_2$—O)$_2$—$C_{10}H_{21}$, HO—$(CH_2$—$CH_2$—O)$_3$—$C_{10}H_{21}$, HO—$(CH_2$—$CH_2$—O)$_4$—$C_{10}H_{21}$, HO—$(CH_2$—$CH_2$—O)$_5$—$C_{10}H_{21}$, HO—$(CH_2$—$CH_2$—O)$_6$—$C_{10}H_{21}$, HO—$(CH_2$—$CH_2$—O)$_7$—$C_{10}H_{21}$, HO—$(CH_2$—$CH_2$—O)$_8$—$C_{10}H_{21}$, HO—$(CH_2$—$CH_2$—O)$_9$—$C_{10}H_{21}$,
HO—$(CH_2$—$CH_2$—O)$_2$—$C_{13}H_{27}$, HO—$(CH_2$—$CH_2$—O)$_3$—$C_{13}H_{27}$, HO—$(CH_2$—$CH_2$—O)$_4$—$C_{13}H_{27}$, HO—$(CH_2$—$CH_2$—O)$_5$—$C_{13}H_{27}$, HO—$(CH_2$—$CH_2$—O)$_6$—$C_{13}H_{27}$, HO—$(CH_2$—$CH_2$—O)$_7$—$C_{13}H_{27}$, HO—$(CH_2$—$CH_2$—O)$_8$—$C_{13}H_{27}$, HO—$(CH_2$—$CH_2$—O)$_9$—$C_{13}H_{27}$,
HO—$(CH_2$—$CH_2$—O)$_2$—$C_{15}H_{31}$, HO—$(CH_2$—$CH_2$—O)$_3$—$C_{15}H_{31}$, HO—$(CH_2$—$CH_2$—O)$_4$—$C_{15}H_{31}$, HO—$(CH_2$—$CH_2$—O)$_5$—$C_{15}H_{31}$, HO—$(CH_2$—$CH_2$—O)$_6$—$C_{15}H_{31}$, HO—$(CH_2$—$CH_2$—O)$_7$—$C_{15}H_{31}$, HO—$(CH_2$—$CH_2$—O)$_8$—$C_{15}H_{31}$ or HO—$(CH_2$—$CH_2$—O)$_9$—$C_{15}H_{31}$.

The amount of alcohol may be at least 0.1% by volume, preferably 10 to 500% by volume, more preferably 15 to 300% by volume and most preferably 50 to 200% by volume of the silane components used.

The amount of alcohol may be at least 0.1% by weight, preferably 10 to 500% by weight, more preferably 15 to 200% by weight, even more preferably 25 to 100% by weight and exceptionally preferably 25 to 50% by weight of the (haloorganyl)alkoxysilanes of the formula II used.

The alcohols used may be mixtures of alcohols.

The alcohol used may comprise water.

The alcohol can be obtained from an alcohol-water mixture by distillation as an azeotrope.

The alcohol used may contain 1-80% by weight, preferably 5-60% by weight, more preferably 7-40% by weight, even more preferably 8-30% by weight and exceptionally preferably 10-20% by weight of water.

The alcohol may contain less than 50% by weight, preferably less than 40% by weight, more preferably less than 30% by weight and especially preferably less than 20% by weight of water.

The reaction can be effected at temperatures between 0 and 180° C., preferably between 30 and 150° C., more preferably between 50 and 100° C.

The process according to the invention can be carried out in an open or closed vessel.

The process according to the invention can be carried out in such a way that a gas which forms cannot escape from the reaction chamber.

The reaction can preferably be carried out in a closed vessel.

The closed vessel may preferably be a reaction vessel known from industry, which allows working at pressures up to 20 bar and temperatures up to 200° C.

The closed vessel may more preferably be a reaction vessel known from industry, which allows working at pressures up to 6 bar and temperatures up to 150° C.

The closed vessel may possess a heating/cooling circuit.

The reaction and workup can preferably be effected in corrosion-resistant reaction vessels or autoclaves, for example made of glass, Teflon, plastic materials, enamelled or coated steel, stainless steel, Hastelloy or tantalum.

The reaction in the preparation of organosilanes of the general formula I can be carried out under an elevated pressure of 0.1 bar to 20 bar, preferably of 0.1 bar to 15 bar, more preferably of 0.5 bar to 10 bar and most preferably of 0.5 bar to 6 bar.

The pressure in the reaction vessel may depend on the fill height in the reaction vessel. High fill levels can maintain the pressure in the reaction vessel during the reaction at <6 bar, preferably <5 bar, more preferably <4 bar.

The reaction can preferably be carried out with exclusion of air.

Compounds of the general formula I can preferably be prepared in an alcohol in a closed vessel in the presence of $H_2S$.

Compounds of the general formula I can preferably be prepared in an alcohol in a closed vessel and under elevated pressure in the presence of $H_2S$.

The workup of the crude product suspensions may include a filtration and removal of solid constituents.

The workup of the crude product suspension may include a distillation and removal of volatile constituents.

The workup of the crude product suspension may first include a distillation and then a filtration.

The workup of the crude product suspension may first include a filtration and then a distillation.

The workup of the crude product suspension may first include a filtration, then a distillation and then a further filtration.

The workup of the crude product suspension may first include a distillation, then a filtration and then a further treatment under elevated temperature and under reduced pressure.

To work up the crude product suspension, the alcohol/water mixture can be removed and the product of the general formula I formed can then be removed from the solids.

To work up the crude product suspension, the solids can be removed and then an alcohol/water mixture can be removed from the product of the general formula I formed. The alcohol/water mixture can be removed from the product of the general formula I formed by distillation or phase separation.

To work up the crude product suspension, the alcohol/water mixture can be removed, and the remaining crude product suspension comprising the organosilicon compound of the general formula (I) and alkali metal halide can be mixed with water and the phases which form can be separated.

The salt-containing crude product suspension present after the reaction can be worked up at standard pressure or under reduced pressure, preferably under a reduced pressure between 1 and 600 mbar, more preferably between 5 and 250 mbar, most preferably between 10 and 100 mbar.

During the workup of the crude products, aqueous alcohol can be removed under reduced pressure and at elevated temperature.

During the workup of the crude products, aqueous alcohol can be removed under reduced pressure and under elevated temperature such that, during the first hour of the distillation, 0.1 to 75% by weight, preferably 5 to 60% by weight, more preferably 5 to 50% by weight and most preferably 10 to 40% by weight of the aqueous alcohol is removed.

During the workup of the crude products, aqueous alcohol can be removed under reduced pressure and under elevated temperature such that, during the second hour of the distillation, 5 to 70% by weight, preferably 10 to 60% by weight, more preferably 15 to 50% by weight and most preferably 20 to 45% by weight of the aqueous alcohol is removed.

It is possible to add and use water-entraining substances (azeotroping agents) known to those skilled in the art.

For the removal of alcohol, azeotroping agents and water, it is possible to use assistants and apparatus known to those skilled in the art.

The alcohol/water mixture may contain ethanol.

It may be preferable to use vertical tube evaporators, horizontal tube evaporators, circulation evaporators, inclined tube evaporators, falling-film evaporators, plate evaporators, blast pipe evaporators, rotary evaporators, centrifugal evaporators, screw evaporators, thin-layer evaporators and thin-film strippers for the removal of alcohol, azeotroping agent and water.

The salt-containing product suspension present after the reaction can be worked up at temperatures between 0 and 200° C., preferably between 5 and 100° C., more preferably between 10 and 70° C., most preferably between 20 and 60° C.

The crude product suspension formed may comprise alkali metal halides, for example NaCl, alkali metal hydrogen-carbonates, for example $NaHCO_3$, and organosilanes of the general formula I.

The alcohol can be removed from the crude product suspension, and the remaining mixture comprising the compound or compounds of the general formula I and alkali metal halide can be mixed with water and the phases which form can be separated. The suspension formed may comprise alkali metal halides, for example NaCl, alkali metal hydrogencarbonates, for example $NaHCO_3$, and compounds of the general formula I.

The product can separate out of the salt-containing water phase by phase separation after the reaction. After the phase separation, the product can be removed from the salt-containing water phase. After the removal of the salt-containing phase, the product can be dried.

The alcohol can be removed from the crude product suspension, the mixture comprising the compounds of the general formula I and alkali metal halide can be mixed with water, and the phases which form can be separated.

Additional water can be added to a mixture of product and solid, with or without alcohol and/or water.

In the course of workup, water can be added in an amount of 1 to 500% by weight, preferably 1 to 300% by weight, more preferably 5 to 150% by weight, most preferably 5 to 75% by weight, based on the compound or compounds of the formula I.

In the workup, the water added may be deionized water. In the workup, the water added may contain a buffer, for example sodium hydrogencarbonate and/or sodium carbonate. The buffer content of the water may be 1% by weight to 20% by weight, preferably 2% by weight to 10% by weight, more preferably 2% by weight to 5% by weight.

The water added may have a pH between 3 and 11, preferably between 4 and 10, more preferably between 5 and 9.5, most preferably between 7 and 9.5.

The pH of the water added can be adjusted by means of a buffer.

The crude product yield of the process according to the invention may be greater than 70%, preferably greater than 80%, more preferably greater than 85%, most preferably greater than 90%, based on the theoretical yield with regard to the amount of (haloorganyl)alkoxy-silane of the formula II used.

The crude product yield may be the gravimetrically determined sum of all isolated liquid compounds once alcohol, water and solids have been removed.

The amount of $H_2S$ released during the reaction can be determined after or actually during the reaction. For the quantitative determination, the $H_2S$ can be passed, for example, through a copper sulphate or lead acetate solution, and the precipitated solid can be determined gravimetrically.

The amount of $H_2S$ may, at the end of the reaction, based on the amount of alkali metal carbonate used, be less than 50 mol %, preferably less than 30 mol %, more preferably less than 20 mol %, most preferably less than 10 mol %.

The amount of $H_2S$ may, at the end of the reaction, based on the amount of alkali metal hydrogensulphide used, be less than 50 mol %, preferably less than 30 mol %, more preferably less than 20 mol %, most preferably less than 10 mol %.

The amount of $H_2S$ may, at the end of the reaction, based on the molar amount of organosilane of the formula II used, be less than 50 mol %, preferably less than 30 mol %, more preferably less than 20 mol %, most preferably less than 10 mol %.

A minimization of the amount of $H_2S$ released in the course of the reaction may be advantageous.

The mixture of appropriate (haloorganyl)alkyloxysilane and additives used may, depending on the apparatus used and the desired effects, some of which can be influenced independently, for example selectivity of the reaction, duration of the reaction, reactor throughput, reaction of (haloorganyl)alkyloxysilane and sulphurizing reagent with one another, value of m, reaction of alkali metal hydrogensulphide and sulphur, the reactor material or the process sequence, be prepared actually before the addition of the sulphurizing reagents.

The mixture of alkali metal hydrogensulphide, sulphur, alkali metal carbonate and additives used may, depending on the apparatus used and the desired effects, some of which can be influenced independently, be prepared actually before the addition of the (haloorganyl)alkoxysilane.

The (haloorganyl)alkoxysilane and the additives may be mixed with one another in any sequence, manner, temperature and duration, and only then are the alcohol and alkali metal hydrogensulphide, sulphur and alkali metal carbonate added together or successively.

Additives, alkali metal hydrogensulphide, sulphur and alkali metal carbonate and alcohol can be mixed with one another in any sequence, manner, temperature and duration, and only then is the (haloorganyl)alkoxysilane added.

The (haloorganyl)alkoxysilane, alkali metal hydrogen-sulphide, sulphur and alkali metal carbonate and alcohol may be mixed with one another in any sequence, manner, temperature and duration, and only then are additives added.

The (haloorganyl)alkoxysilane, alkali metal hydrogen-sulphide, sulphur and alkali metal carbonate and additives may be mixed with one another in any sequence, manner, temperature and duration, and only then is alcohol added.

Alkali metal hydrogensulphide, sulphur and alkali metal carbonate and additives may be mixed with one another in any sequence, manner, temperature and duration, and only then are the alcohol and (haloorganyl)alkoxysilane added together or successively.

Hydrous alkali metal hydrogensulphides may be added independently to the reaction mixture before and/or during the reaction.

The hydrous alkali metal hydrogensulphides may independently be mixed with sulphur or $H_2S$ and be added to the reaction mixture before, during or at the end of the reaction.

The amount of by-products may be less than 40% by weight, preferably less than 30% by weight, more preferably less than 20% by weight and most preferably less than 15% by weight, based on the amount of organosilane of the formula I.

One of the by-products may be (mercaptoorganyl)alkoxysilane.

The (mercaptoorganyl)alkoxysilane content may be less than 10% by weight, preferably less than 4% by weight, more preferably less than 2% by weight and most preferably less than 1.5% by weight, in the end product.

The amount of (mercaptoorganyl)alkoxysilane may be determined by 1H NMR, 29Si NMR, 13C NMR or gas chromatography.

The determination of the amount of (mercaptoorganyl) alkoxysilane by gas chromatography with dodecane as the internal standard is preferred.

The residual amount of (haloorganyl)alkoxysilane reactant may, through selection of the reaction conditions (for example reaction time and temperature), be less than 15% by weight, preferably less than 10% by weight, more preferably less than 5% by weight and most preferably less than 3% by weight.

The residual amount of (haloorganyl)alkoxysilane reactant may be 0.5 to 5% by weight, preferably 1 to 4% by weight, more preferably 1 to 3% by weight and most preferably 1 to 2% by weight.

The residual amount of (haloorganyl)alkoxysilane reactant may be determined by 1H-NMR, 29Si-NMR, 13C-NMR or gas chromatography.

The determination of the residual amount of reactant by gas chromatography with dodecane as the internal standard is preferred.

The residual amount of reactant can be measured by gas chromatography based on "Standard test Method for Silanes Used in Rubber Formulations (Bis-(triethoxy-silylpropyl)sulfanes): Characterization by Gas Chromatography (GC), D 6843-02".

Advantages of the process according to the invention are the high conversion coupled with good selectivity, lack of use of solid alkali metal sulphide hydrate and the minor influence of the amount of alkali metal hydroxide.

EXAMPLES

GC Analysis

The GC analysis of the isolated crude products is carried out on a gas chromatograph (FID) with dodecane as the internal standard.

The gas chromatography analyses of the examples are carried out as described in "Standard test Method for Silanes Used in Rubber Formulations (Bis-(triethoxysilylpropyl)sulfanes): Characterization by Gas Chromatography (GC), D 6843-02".

HPLC Analysis:

The method of HPLC analysis is described in "Luginsland, H-D., Reactivity of the Sulfur Functions of the Disulfane Silane TESPD and Tetrasulfane Silane TESPT, paper presented at the ACS Meeting, April 1999, Chicago".

The mean sulphur chain length is calculated as follows:

$$m = \frac{\sum_{i=2}^{10} i \cdot A_i \cdot R_i / M_i}{\sum_{i=2}^{10} A_i \cdot R_i / M_i}$$

m=mean sulphur chain length
i=number of sulphur atoms in the silane component
$M_i$=molar mass of the silane component with i sulphur atoms
$A_i$=area of the signal of the silane component with i sulphur atoms
$R_i$=response factor of the sulphur silane component with i sulphur atoms If organosilanes of the formula I contain compounds with $S_1$, the mean sulphur chain length is corrected taking account of the molecular weights.

$^{29}$Si NMR:

The Si spectra are recorded on a Bruker Avance 500 NMR spectrometer with a measurement frequency for Si of 99.35 MHz (H NMR 500.13 MHz). The spectra are referenced internally against tetramethylsilane (TMS=0 ppm). The samples are analysed as an approx 30% solution in $CDCl_3$ with addition of chromium acetylacetonate (approx. 0.05 to 0.1 molar solution) as a relaxation accelerant. The pulse sequence used is an inverse-gated sequence with proton decoupling only during the acquisition time and a relaxation delay of 5 s.

Example 1

In a pressure-resistant reactor,
50 kg of NaSH hydrate from ICS-Chemie Wolfen with a purity of 69±1% by weight (in the solid), 0.67% by weight NaOH content (in solution) and 25% by weight water content,
74.8 kg of $Na_2CO_3$ from Solvay with a particle distribution (median) by laser diffraction of 384 μm,
20 kg of sulphur powder (ground sulphur) from CS Additive with a particle distribution (median) by laser diffraction of 17 μm,
193 kg of ethanol and 34 kg of water are mixed with one another.
269 kg of (3-chloropropyl)triethoxysilane from Evonik-Degussa GmbH (22 ppm of hydrolysable chloride) are metered into the reactor at 55° C. within 30 min in such a way that gas which forms cannot escape. Subsequently, the reaction mixture is heated in the closed reactor at 70-80° C. for 80 min and at 70° C. for 130 min. After the reaction, the solvent is removed under reduced pressure at elevated temperature. In the first hour 11% and in the second hour 21% of the total amount of solvent mixture isolated is removed under reduced pressure. The salts are removed with a centrifuge. 242 kg of liquid, clear product are isolated.
Composition:

| | |
|---|---|
| average S chain length m (HPLC) | 2.17 |
| (3-chloropropyl)triethoxysilane (GC) | 1.9% by weight |
| (3-mercaptopropyl)triethoxysilane (GC) | 1.2% by weight |
| $(EtO)_3Si$—$(CH_2)_3$—$S_2$—$(CH_2)_3$—$Si(OEt)_3$ (HPLC; S2-S10) | 83.4% |
| $(EtO)_3Si$—$(CH_2)_3$—$S_3$—$(CH_2)_3$—$Si(OEt)_3$ (HPLC; S2-S10) | 15.4% |

Example 2

In a pressure-resistant reactor, 85.6 g of NaSH solution from Akzo Nobel with an NaSH content of 45.5% by weight,
75 g of $Na_2CO_3$ from Merck with a particle size distribution (median) according to laser diffraction of 360 μm,
57.1 g of sulphur pellets from Kemmax with a particle size distribution (median) of >1 mm,
153 g of ethanol and 17 g of water are mixed with one another.
330 g of (3-chloropropyl)triethoxysilane from Evonik-Degussa GmbH (102 ppm of hydrolysable chloride) are metered into the reactor at 65-75° C. within 60 min in such a way that gas which forms cannot escape. Subsequently, the reaction mixture is heated at 75° C. in the closed reactor for 150 min. After the reaction, the solvent is removed under reduced pressure at 105° C. within 3 h. After the solvent removal has ended, the salt is removed by filtration. 212.4 g of liquid, clear product are isolated. Washing the salt with solvent and subsequent workup allows a further 86.3 g of product to be isolated.
Composition of the Isolated Product:

| | |
|---|---|
| average S chain length m (HPLC; S2-S10) | 3.73 |
| (3-chloropropyl)triethoxysilane (GC) | <0.5% by weight |
| (3-mercaptopropyl)triethoxysilane (GC) | 0.75% by weight |
| $(EtO)_3Si$—$(CH_2)_3$—$S_2$—$(CH_2)_3$—$Si(OEt)_3$ (HPLC; S2-S10) | 18.9% |
| $(EtO)_3Si$—$(CH_2)_3$—$S_3$—$(CH_2)_3$—$Si(OEt)_3$ (HPLC; S2-S10) | 28.7% |
| $(EtO)_3Si$—$(CH_2)_3$—$S_4$—$(CH_2)_3$—$Si(OEt)_3$ (HPLC; S2-S10) | 23.4% |

Example 3

In a pressure-resistant reactor, 96 g of NaSH solution from Akzo Nobel with an NaSH content of 45.5% by weight,
75 g of $Na_2CO_3$ from Merck with a particle size distribution (median) according to laser diffraction of 360 μm,
29.1 g of sulphur pellets from Kemmax with a particle size distribution (median) of >1 mm,
150 g of ethanol and 20 g of water are mixed with one another.
300 g of (3-chloropropyl)triethoxysilane from Evonik-Degussa GmbH (102 ppm of hydrolysable chloride) are metered into the reactor at 65-75° C. within 60 min in such a way that gas which forms cannot escape. Subsequently, the reaction mixture is heated in the closed reactor at 75° C. for 180 min. After the reaction, the solvent is removed under reduced pressure at 105° C. within 3 h, in the course of which the pressure was standard pressure for 60 min, 860 mbar for 60 min and 80 mbar for 60 min. After the solvent removal has ended, the salt is removed by filtration. Including the washing of the salt with 3×200 ml of solvent plus distillation thereof, a total of 300.1 g of liquid, clear product is isolated.
Composition of the Isolated Product:

| | |
|---|---|
| average S chain length m (HPLC; S2-S10) | 2.44 |
| (3-chloropropyl)triethoxysilane (GC) | 0.6% by weight |
| (3-mercaptopropyl)triethoxysilane (GC) | 0.76% by weight |
| $(EtO)_3Si$—$(CH_2)_3$—$S_2$—$(CH_2)_3$—$Si(OEt)_3$ (HPLC; S2-S10) | 62.8% |
| $(EtO)_3Si$—$(CH_2)_3$—$S_3$—$(CH_2)_3$—$Si(OEt)_3$ (HPLC; S2-S10) | 29.5% |

-continued

| | |
|---|---|
| (EtO)₃Si—(CH₂)₃—S₄—(CH₂)₃—Si(OEt)₃ (HPLC; S2-S10) | 6.5% |

Example 4

In a pressure-resistant reactor, 55 g of NaSH from ICS with an NaSH content of 71% by weight, 75 g of Na₂CO₃ from Merck, 21.9 g of sulphur powder (ground sulphur) with a particle size distribution (median) of 41 μm according to laser diffraction, 128 g of ethanol and 32 g of water are mixed with one another.

300 g of (3-chloropropyl)triethoxysilane from Evonik-Degussa GmbH (42 ppm of hydrolysable chloride) are metered into the reactor at 70° C. within 7 min in such a way that gas which forms cannot escape. Subsequently, the reaction mixture is heated in the closed reactor at 80° C. for 145 min.

Thereafter, the internal pressure is increased to 2.5 bar at 50° C. with gaseous CO₂ (Aldrich) and the suspension is stirred for 10 min under pressure.

The elevated pressure is then released and the suspension is filtered. 30 g of water are added to the filtrate, the mixture is stirred for a further 15 min and then the two liquid phases are separated from one another.

The organic phase is freed of solvent residues at 95° C. to isolate 190.9 g of liquid clear product. It was possible to recover a further 70 g of product from the salt by washing with 200 g of solvent. The handling losses and product residues on the salt in this experiment are estimated at approx. 25 g.

Composition of the Isolated Product:

| | |
|---|---|
| average S chain length m (HPLC; S2-S10) | 2.24 |
| (3-chloropropyl)triethoxysilane (GC) | 2% by weight |
| (EtO)₃Si—(CH₂)₃—S₂—(CH₂)₃—Si(OEt)₃ (HPLC; S2-S10) | 77.1% |
| (EtO)₃Si—(CH₂)₃—S₃—(CH₂)₃—Si(OEt)₃ (HPLC; S2-S10) | 20.5% |
| (EtO)₃Si—(CH₂)₃—S₄—(CH₂)₃—Si(OEt)₃ (HPLC; S2-S10) | 2.3% |

Example 5

In a pressure-resistant reactor, 85.6 g of aqueous NaSH solution from Akzo Nobel with an NaSH content of 45.5% by weight, 75 g of Na₂CO₃ from BASF, 57.1 g of sulphur pellets from Kemmax with a particle size distribution (median) of >1 mm, 146.2 g of ethanol and 23.8 g of water are mixed with one another.

330 g of (3-chloropropyl)triethoxysilane from Evonik-Degussa GmbH (102 ppm of hydrolysable chloride) are metered into the reactor at 65-75° C. within 60 min in such a way that gas which forms cannot escape. Subsequently, the reaction mixture in the closed reactor is heated at 75° C. for 150 min.

The elevated pressure is then released and the suspension is filtered. The two liquid phases obtained are separated from one another. The salt is washed with 170 g of ethanol (water content 15%) and the filtrate is then combined with the liquid organic phase.

The combined organic phases are freed of solvent residues at 40° C./20 mbar to isolate 335.8 g of liquid product.

It was possible to isolate further product from the salt by extraction.

Composition of the Isolated Product:

| | |
|---|---|
| average S chain length m (HPLC; S2-S10) | 3.62 |
| (3-chloropropyl)triethoxysilane (GC) | 0.7% by weight |
| (3-mercaptopropyl)triethoxysilane (GC) | 0.8% by weight |
| (EtO)₃Si—(CH₂)₃—S₂—(CH₂)₃—Si(OEt)₃ (HPLC; S2-S10) | 17.8% |
| (EtO)₃Si—(CH₂)₃—S₃—(CH₂)₃—Si(OEt)₃ (HPLC; S2-S10) | 20.5% |
| (EtO)₃Si—(CH₂)₃—S₄—(CH₂)₃—Si(OEt)₃ (HPLC; S2-S10) | 2.3% |

We claim:

1. Process for preparing organosilanes of the general formula I

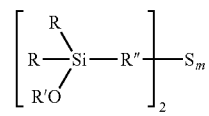

I where
R is the same or different and is a $C_1$-$C_8$-alkyl, $C_1$-$C_8$-alkenyl, $C_1$-$C_8$-aryl or $C_1$-$C_8$-aralkyl group or an OR' group,
R' is the same or different and is a $C_1$-$C_{24}$ branched or unbranched monovalent alkyl or alkenyl group, an aryl group, an aralkyl group, hydrogen, an alkyl ether group —$(CR^{III}_2)_{y'}$—O-Alk, where y'=1-20, or an alkyl polyether group —$(CR^{III}_2O)_y$-Alk or —$(CR^{III}_2$—$CR^{III}_2$—$O)_y$-Alk, where y=2-20, $R^{III}$ is independently H or an alkyl group and Alk is a branched or unbranched, saturated or unsaturated, aliphatic, aromatic or mixed aliphatic/aromatic monovalent $C_1$-$C_{30}$ hydrocarbon group,
R" is a branched or unbranched, saturated or unsaturated, aliphatic, aromatic or mixed aliphatic/aromatic divalent $C_1$-$C_{30}$ hydrocarbon group which is optionally substituted by F, Cl, Br, I, HS, $NH_2$ or NHR',
m is a mean sulphur chain length of 1.5 to 4.5,
by reacting (haloorganyl)alkoxysilane of the formula II

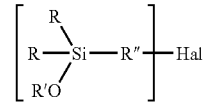

II where R, R' and R" are each as defined above and Hal is chlorine, bromine, fluorine or iodine, with hydrous alkali metal hydrogensulphide, sulphur and alkali metal carbonate in alcohol, wherein the molar (haloorganyl)alkoxysilane of the formula II to alkali metal hydrogensulphide ratio is between 1:0.45 and 1:0.75, and the molar alkali metal hydrogensulphide to alkali metal carbonate ratio is between 1:0.5 and 1:1.5.

2. Process for preparing organosilanes according to claim 1, wherein additives are added before, during or after the reaction.

3. Process for preparing organosilanes according to claim 2, wherein the additives are nonalcoholic solvents or polar, protic, aprotic, basic or acidic additives.

4. Process for preparing organosilanes according to claim 1, wherein an alcohol/water mixture is removed from the crude product suspension and the product of the general formula I formed is then removed from the solids.

5. Process for preparing organosilanes according to claim 1, wherein the solids are removed from the crude product suspension and then an alcohol/water mixture is removed from the product of the general formula I formed.

6. Process for preparing organosilanes according to claim 5, wherein an alcohol/water mixture is removed from the product of the general formula I formed by distillation.

7. Process for preparing organosilanes according to claim 5, wherein an alcohol/water mixture is removed from the product of the general formula I formed by phase separation.

8. Process for preparing organosilanes according to claim 1, wherein an alcohol/water mixture is removed from the crude product suspension, and the remaining crude product suspension comprising the organosilicon compound of the general formula (I) and alkali metal halide is mixed with water and the phases which form are separated.

* * * * *